United States Patent [19]

Becker et al.

[11] Patent Number: 4,728,357
[45] Date of Patent: Mar. 1, 1988

[54] CYCLOHEXANE-1,3-DIONE DERIVATIVES, THEIR PREPARATION AND HERBICIDES CONTAINING THESE COMPOUNDS

[75] Inventors: Rainer Becker, Bad Duerkheim; Dieter Jahn, Edingen-Neckarhausen; Wolfgang Rohr, Wachenheim; Bruno Wuerzer, Otterstadt, all of Fed. Rep. of Germany

[73] Assignee: BASF Aktiengesellschaft, Ludwigshafen, Fed. Rep. of Germany

[21] Appl. No.: 759,925

[22] Filed: Jul. 29, 1985

Related U.S. Application Data

[63] Continuation of Ser. No. 515,897, Jul. 21, 1983, abandoned.

[30] Foreign Application Priority Data

Jul. 22, 1982 [DE] Fed. Rep. of Germany ....... 3227389

[51] Int. Cl.$^4$ ...................... A01N 31/06; C07C 83/06
[52] U.S. Cl. ....................................... 71/98; 564/300
[58] Field of Search ................. 564/256, 300; 71/98

[56] References Cited

U.S. PATENT DOCUMENTS 4,249,937  2/1981  Iwataki et al. .................... 564/256

FOREIGN PATENT DOCUMENTS 2077732  12/1981  United Kingdom .

Primary Examiner—James H. Reamer
Attorney, Agent, or Firm—Keil & Weinkauf

[57] ABSTRACT

Cyclohexane-1,3-dione derivatives of the formula

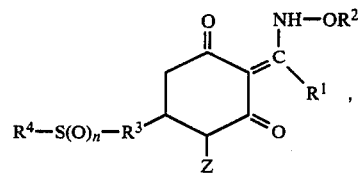

where $R^1$ is alkyl of from 2 to 4 carbon atoms, $R^2$ is alkyl, unsubstituted or halogen-substituted alkenyl, or alkynyl, each of from 2 to 5 carbon atoms, $R^3$ is a saturated or unsaturated hydrocarbon radical of up to 4 carbon atoms which is unsubstituted or substituted by 1 to 3 hydrocarbon radicals of a total of up to 8 carbon atoms, by aryl of from 6 to 10 carbon atoms, or by benzyl, $R^4$ is, when $R^3$ is unsaturated or olefinically or aromatically substituted, alkyl of from 1 to 6 carbon atoms, $R^4$ is further unsubstituted or halogen-substituted alkenyl of from 2 to 6 carbon atoms, alkynyl of from 2 to 6 carbon atoms, naphthyl, arylalkyl or arylalkenyl, where aryl is of from 6 to 10 carbon atoms and is unsubstituted or substituted by alkyl or alkoxy, each of from 1 to 3 carbon atoms, or by halogen, and where alkyl or alkenyl is of from 2 to 3 carbon atoms, at least 2 of which being between aryl and sulfur, Z is H, CN, CH$_3$, methoxycarbonyl or ethoxycarbonyl, and n is 0,1 or 2, and salts thereof.

3 Claims, No Drawings

CYCLOHEXANE-1,3-DIONE DERIVATIVES, THEIR PREPARATION AND HERBICIDES CONTAINING THESE COMPOUNDS

This application is a continuation of application Ser. No. 515,897, filed on July 21, 1983, now abandoned.

It has been disclosed that, for example, 2-(1-ethoxyaminobutylidene)-5-(2-ethylthiopropyl)-cyclohexane-1,3-dione and other compounds of this type possessing a lower alkyl or phenyl group at the sulfur atom have a good action against grasses (U.S. Pat. No. 4,249,937 and British Pat. No. 2,090,246).

We have found that the compounds as claimed in claim 1 likewise have a herbicidal action against grasses, and moreover cause little or no damage either to broadleaved crop plants and monocotyledon crops, which do not belong to the family of grasses (Gramineae), or, surprisingly, to cereals.

The novel compounds of the formula I can occur in various tautomeric forms, all of which are embraced by the claims:

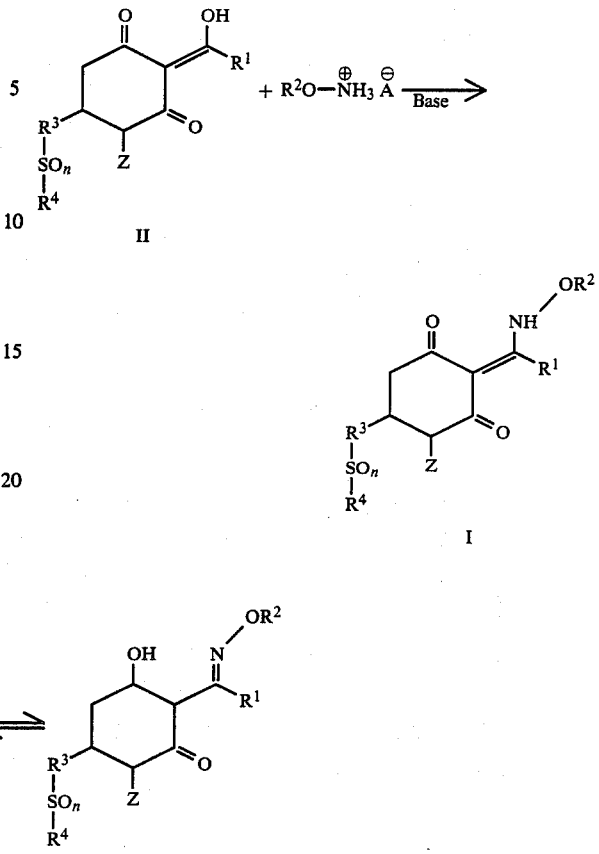

In formula I $R^1$ is branched or straight-chain alkyl of 2 to 4 carbon atoms, e.g. ethyl, n-propyl, i-propyl or n-butyl, $R^2$ is alkyl or alkenyl of 2 or 3 carbon atoms, for example ethyl, allyl, n-propyl, i-propyl, $R^3$ is ethylene which is unsubstituted or substituted by 1 to 2 substituents selected from the group consisting of methyl, phenyl, benzyl and $C_2$-$C_6$-alkenyl, the substituents totaling a maximum of 7 carbon atoms, or $R^3$ is propenylene, $R^4$ is, when $R^3$ is unsaturated or olefinically or aromatically substituted, alkyl of from 1 to 6 carbon atoms, $R^4$ is further alkenyl of from 2 to 6 carbon atoms, phenyl, chlorophenyl, naphthyl or phenylethyl, Z=H, and n i O, or a salt thereof.

Examples of suitable salts of the compounds of the formula I are the alkali metal salts, in particular potassium or sodium salts, alkaline earth metal salts, in particular calcium, magnesium or barium salts, and manganese salts, copper salts, zinc salts and iron salts.

The anion $A^\ominus$ of the hydroxylammonium salt referred to in claim 2 is a monovalent anion or one equivalent of a polyvalent anion, e.g. $Cl^-$, $Br^-$, $\frac{1}{2} SO_4^{--}$ or $H_3C-COO^-$.

Preparation

The novel derivatives I can be prepared by the methods described below:

In the formulae, $R^1$, $R^2$, $R^3$, $R^4$, Z and A have the above meanings.

The reaction is advantageously carried out in the heterogeneous phase at from 0° to 80° C. in an inert solvent in the presence of a base. Examples of suitable bases are carbonates, bicarbonates, acetates, alcoholates, hydroxides or oxides of alkali metals or alkaline earth metals, in particular of sodium, potassium, magnesium or calcium. Organic bases, e.g. pyridine or tertiary amines, may also be used. A defined pH of from 2 to 8, in particular from 4.5 to 5.5, is particularly suitable for the reaction, this pH advantageously being established by the addition of an acetate, eg. sodium acetate or potassium acetate, or of a bicarbonate, eg. sodium bicarbonate or potassium bicarbonate. The base is used in an amount of from 0.5 to 2 moles, based on the hydroxylammonium compound. Examples of suitable solvents are dimethylsulfoxide, alcohols, such as methanol, ethanol and isopropanol, benzene, toluene, hydrocarbons and chlorohydrocarbons, such as methylene chloride, chloroform or dichloroethane, esters, such as ethyl acetate, and ethers, such as dioxane, tetrahydrofuran or diethyl ether. The reaction is complete after a few hours, and the product can be obtained by evaporating down the reaction mixture, adding water, extracting the mixture with a non-polar solvent, eg. methylene chloride, and distilling off the solvent under reduced pressure.

The compounds of the formula I can also be obtained by reacting a compound II with a hydroxylamine of the formula $R^2ONH_2$, or an aqueous solution of this, in an inert solvent under the conditions described above.

Furthermore, the novel compounds can be prepared by reacting a compound of the formula II with hydroxylamine to give an oxime, and alkylating the latter with a suitable alkylating agent to give the novel end product:

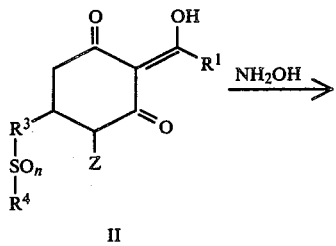

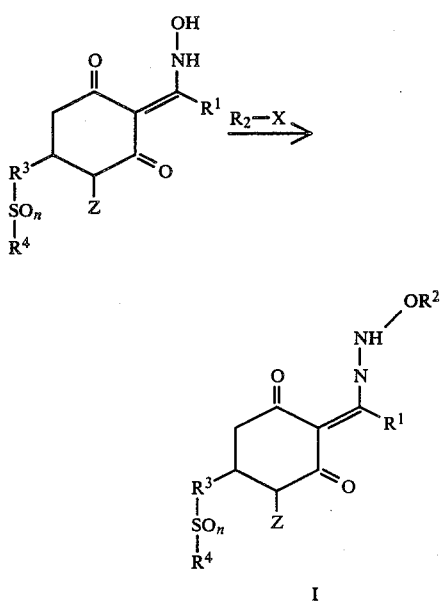

The compounds of the formula II can be obtained by C-acylation of a cyclohexane-1,3-dione(III), as described in Tetrahedron Lett. (1975), page 2491. In another suitable method of preparing the derivatives II, a cyclohexane-1,3-dione (III) is C-acylated and the product is then subjected to a rearrangement reaction under acid catalysis (AlCl$_3$, as described in Synthesis (1978), page 925) or base catalysis (pyridine derivatives, as described in Japanese Pat. No. 54,063,052).

The compounds III can also occur in the tautomeric forms III a/b shown below:

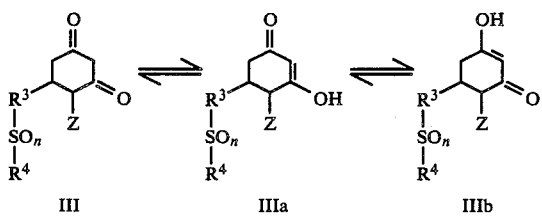

Compounds of the formula III can be prepared from an aldehyde $R^4$—$SO_n$—$R^3$—CH=O by a conventional method, for example by aldol condensation with acetone followed by cyclisation with a malonate by a procedure similar to that described in Organic Synthesis Coll. Vol. II, page 200. The intermediates of the formula III can also be obtained by reacting an aldehyde $R^4SO_nR^3$—CHO with malonic acid by the Knoevenagel-Doebner reaction (cf. Org. Reaction Vol. 15, page 204), esterifying the resulting acid and subjecting the product to a cyclization reaction with ethyl acetoacetate, the procedure used being similar to that described in, for example, Chem. Ber. 96 (1963), page 2946.

The aldehydes $R^4$—$SO_n$—$R^3$CHO can be obtained by an addition reaction of a mercaptan with an unsaturated aldehyde (German Pat. No. 855,704). Another possible method of synthesizing the compounds III comprises reacting a γ-halocrotonic acid derivative with a mercaptan and subjecting the resulting γ-mercaptocrotonic acid derivative to a cyclization reaction with ethyl acetoacetate, as described above.

The sodium and potassium salts of the novel compounds can be obtained by treating these compounds with sodium hydroxide or potassium hydroxide in aqueous solution or in an organic solvent, e.g. methanol, ethanol or acetone. The base used may also be an alkali metal alcoholate.

Other metal salts, e.g. the manganese, copper, zinc, iron or barium salts, can be prepared by reacting the sodium salt with the appropriate metal chloride in aqueous solution.

The Examples which follow illustrate the preparation of the novel cyclohexanediones. Parts are by weight, and parts by weight bear the same relation to parts by volume as that of the kg to the liter.

EXAMPLE 1

10.6 parts by weight of 2-butyryl-4-methoxycarbonyl-5-(2-allylthiopropyl)-cyclohexane-1,3-diol are dissolved in 150 parts by volume of ethanol, 3.3 parts by weight of allyloxiammonium chloride and 2.9 parts by weight of sodium acetate are added and the mixture is stirred for 20 hours at room temperature. Thereafter, the mixture is poured into ice water, the resulting mixture is extracted with methylene chloride and the latter is stripped off to give 11.3 g of 2-(1-allyloxibutylidene)-4-methoxycarbonyl-5-(2-allylthiopropyl)-cyclohexane-1,3-dione as a yellow oil.

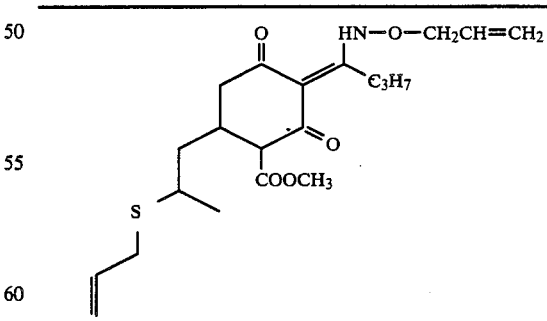

| | | | | |
|---|---|---|---|---|
| $C_{21}H_{31}NO_5S$ | M = 409 | $n_D^{25}$ 1,5337 | | |
| calculated: | C 61.5 | H 7.6 | N 3.4 | S 7.8 |
| found: | C 61.7 | H 7.7 | N 3.1 | S 8.2 |

The following compounds may be prepared analogously:

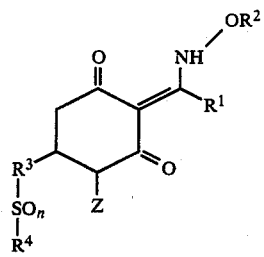

| Compound no. | $R^1$ | $R^2$ | $-R^3-S-$ | $R^4$ | Z | n | Refractive index (°C.) |
|---|---|---|---|---|---|---|---|
| 1 | n-$C_3H_7$ | $-CH_2CH=CH_2$ | $\rangle-CH_2CH(CH_3)-S-$ | $-CH_2CH=CH_2$ | $-COOCH_3$ | 0 | 1.5337 (25) |
| 2 | " | $-C_2H_5$ | " | " | " | 0 | 1.5325 (25) |
| 3 | " | $-C_2H_5$ | " | " | H | 0 | 1.5397 (25) |
| 4 | " | $-CH_2CH=CH_2$ | " | " | H | 0 | 1.5408 (25) |
| 5 | " | $-CH_2CH=CHCl$ | " | " | H | 0 | |
| 6 | " | $-CH_2CCl=CH_2$ | " | " | H | 0 | |
| 7 | " | $-C_2H_5$ | " | " | H | 1 | |
| 8 | " | $-C_2H_5$ | " | " | H | 2 | |
| 9 | " | $-C_2H_5$ | " | $CH_2CH_2C_6H_5$ | $-COOCH_3$ | 0 | |
| 10 | " | $-CH_2CH=CH_2$ | " | " | $-COOCH_3$ | 0 | 1.5556 (25) |
| 11 | " | $-C_2H_5$ | " | " | H | 0 | |
| 12 | " | $-CH_2CH=CH_2$ | $-CH_2CH(CH_3)-$ | $-CH_2CH_2C_6H_5$ | H | 0 | |
| 13 | " | $-CH_2CH=CHCl$ | " | " | H | 0 | |
| 14 | " | $-CH_2CCl=CH_2$ | " | " | H | 0 | |
| 15 | " | $-C_2H_5$ | " | " | H | 1 | |
| 16 | " | $-C_2H_5$ | " | " | H | 2 | |
| 17 | " | $-C_2H_5$ | $-CH_2CH(C_6H_5)-$ | $-C_2H_5$ | H | 0 | 1.5628 (31) |
| 18 | " | $-CH_2CH=CH_2$ | " | " | H | 0 | 2.5662 (31) |
| 19 | " | $-C_2H_5$ | $-CH_2C(CH_3)CH_2CH_2CH=C(CH_3)_2-$ | " | H | 0 | 1.5192 (31) |
| 20 | " | $-CH_2CH=CH_2$ | " | " | H | 0 | |
| 21 | " | $-C_2H_5$ | $-CH_2C(CH_3)CH_2CH_2CH=C(CH_3)_2-$ | $-C_6H_4$ | H | 0 | |
| 22 | " | $-CH_2CH=CH_2$ | " | $-C_6H_5$ | H | 0 | |
| 23 | " | $-C_2H_5$ | " | $p-Cl-C_6H_4$ | H | 0 | |
| 24 | " | $-CH_2CH=CH_2$ | " | $p-Cl-C_6H_4$ | H | 0 | |
| 25 | " | $-CH_2CH=CHCl$ | " | $-C_2H_5$ | H | 0 | |
| 26 | " | $-CH_2CCl=CH_2$ | " | $-C_2H_5$ | H | 0 | |
| 27 | " | $-C_2H_5$ | $-CH=CH-CH_2-$ | $-C_2H_5$ | H | 0 | |
| 28 | " | $-CH_2CH=CH_2$ | $-CH=CH-CH_2-$ | $-C_2H_5$ | H | 0 | |
| 29 | " | $-C_2H_5$ | $-CH_2-CH=CH-$ | $-C_2H_5$ | H | 0 | |
| 30 | " | $-CH_2-CH=CH_2$ | $-CH_2-CH=CH-$ | $-C_2H_5$ | H | 0 | |
| 31 | $C_2H_5$ | $-C_2H_5$ | $-CH_2CH(CH_3)-$ | $-CH_2CH_2C_6H_5$ | H | 0 | |
| 32 | $C_2H_5$ | $-CH_2CH=CH_2$ | $-CH_2CH(CH_3)-$ | $-CH_2CH_2C_6H_5$ | H | 0 | |
| 33 | $C_2H_5$ | $-CH_2CH=CHCl$ | $-CH_2CH(CH_3)-$ | $-CH_2CH_2C_6H_5$ | H | 0 | |
| 34 | $C_2H_5$ | $-CH_2CCl=CH_2$ | $-CH_2CH(CH_3)-$ | $-CH_2CH_2C_6H_5$ | H | 0 | |
| 35 | n-$C_3H_7$ | $-C_2H_5$ | $-CH_2CH(CH_3)-$ | $-CH_2CH_2C_6H_5$ | $-CH_3$ | 0 | |
| 36 | n-$C_3H_7$ | $-C_2H_5$ | $-CH_2CH(CH_3)-$ | $-CH_2CH_2C_6H_5$ | $-CN$ | 0 | |
| 37 | n-$C_3H_7$ | $-C_2H_5$ | $-CH_2-CH(CH_2C_6H_5)-$ | $-C_2H_5$ | H | 0 | |
| 38 | " | " | $-CH_2-CH(CH_3)-$ | $\beta$-naphthyl | H | 0 | 1.5921 (37) |

Application

The agents may be applied pre- or postmergence. Preferably, the novel active ingredients are applied after emergence of the unwanted plants. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The amount of active ingredient applied depends on the time of the year, the objective to be achieved, the plants to be combated, and the growth stage of the plants, and varies from 0.05 to 5 kg/ha.

The influence of representatives of the novel cyclohexane-1,3-dione derivatives on the growth of unwanted and crop plants is demonstrated in greenhouse experiments.

The vessels employed were plastic flowerpots having a volume of 300 cm$^3$, and which were filled with a sandy loam containing about 1.5% humus. The seeds of the test plants were sown shallow, and separately, according to species. For the preemergence treatment, the active ingredients were applied to the surface of the soil immediately after the seeds had been sown. The compounds were emulsified or suspended in water as vehicle, and sprayed through finely distributing nozzles. The application rate was 3.0 kg of active ingredient per hectare. After the agents had been applied, the vessels were lightly sprinkler-irrigated to induce germination and growth and to active the chemical agents. Transparent plastic covers were then placed on the vessels until the plants had taken root. The cover ensured uniform germination of the plants, insofar as this was not impaired by the active ingredients.

For the postemergence treatment, the plants were first grown in the vessels to a height of from 3 to 15 cm, depending on growth form, before being treated. The soybean plants used for the postemergence treatment were grown in a peat-enriched substrate to ensure better growth than is possible in a sandy loam. For this treatment, plants which had been sown directly in the pots and grown there were selected. No covers were placed on the pots in this treatment method. The application rates for postemergence treatment varied from ingredient to ingredient, and were 0.125, 0.25 and 3.0 kg of active ingredient per hectare.

The following compound was used for comparison purposes at a rate of 0.25 kg/ha:

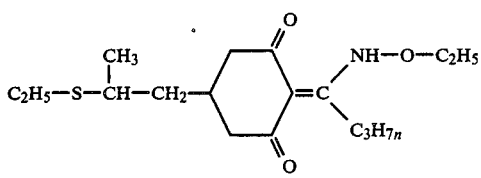

(U.S. Pat. No. 4,249,937)

The following test plants were used in the experiments:

| Botanical name | Common name |
| --- | --- |
| Alopecurus myosuroides | blackgrass |
| Avena fatua | wild oats |
| Echinochloa crus-galli | barnyardgrass |
| Glycine max. | soybeans |
| Lolium multiflorum | Italian ryegrass |
| Hordeum vulgare | barley |
| Triticum aestivum | wheat |
| Oryza sativa | rice |

The pots were set up in the greenhouse—species from warmer areas at from 20° to 35° C., and species from moderate climates at 10° to 20° C. The experiments were run for 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

On pre- and postemergence application in the greenhouse, compounds nos. 3, 4, 11 and 12 had a considerable herbicidal action on grassy species.

In investigations in the greenhouse into selective herbicidal action, compound no. 19 combated unwanted grassy species at 0.25 kg/ha. No damage was inflicted on the soybean plants or on the cereals barley and wheat. The herbicidal action of comparative agent A is somewhat stronger, but even lower (still effective) application rates do not achieve the tolerance of compound no. 19 according to the invention.

On postemergence application in the greenhouse, compound no. 17, at 0.125 kg/ha, exhibited good control of unwanted plants, without damaging crop plants such as soybeans and wheat. The damage caused to *Glycine max.* and *Triticum aestivum* was 0%, to *Alopecurus myosuroides* 80%, and to *Avena fatua* and *Lolium multiflorum* 90%.

Further, compound no. 11, applied postemergence at a rate of 0.06 kg/ha, selectively combated unwanted grasses (88% damage to *Echinochloa crus-galli*) in rice (*Oryza sativa;* 5% damage).

Compound no. 18, applied in the greenhouse at 0.125 kg/ha, controlled wild oats very well (*Avena fatua;* 95% damage) while causing only little damage to wheat (*Triticum aestivum;* 10% damage).

In view of the good tolerance of the herbicides according to the invention, or agents containing them, by numerous broadleaved and other crops, and the numerous application methods possible, they may be used in a large number of crops for removing unwanted plant growth.

The following crops may be mentioned by way of example:

| Botanical name | Common name |
| --- | --- |
| Allium cepa | onions |
| Ananas comosus | pineapples |
| Arachis hypogaea | peanuts (groundnuts) |
| Asparagus officinalis | asparagus |
| Beta vulgaris spp. altissima | sugarbeets |
| Beta vulgaris spp. rapa | fodder beets |
| Beta vulgaris spp. esculenta | table beets, red beets |
| Brassica napus var. napus | rape |
| Brassica napus var. napobrassica | |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass in turf and lawns |
| Daucus carota | carrots |
| Elais guineensis | oil palms |
| Fragaria vesca | strawberries |
| Glycine max | soybeans |
| Gossypium hirsutum (Gossypium arboreum Gossypium herbaceum Gossypium vitifolium) | cotton |
| Helianthus annuus | sunflowers |
| Helianthus tuberosus | |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicothiana tabacum (N. rustica) | tobacco |
| Olea europaea | olive trees |
| Oryza sativa | rice |
| Phaseolus lunatus | limabeans |
| Phaseolus mungo | mungbeans |
| Phaseolus vulgaris | snapbeans, green beans, dry beans |
| Pennisetum glaucum | |
| Petroselinum crispum spp. tuberosum | parsley |
| Picea abies | Norway spruce |
| Abies alba | fir trees |
| Pinus spp. | pine trees |
| Pisum sativum | English peas |

| Botanical name | Common name |
|---|---|
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Sesamum indicum | sesame |
| Solanum tuberosum | Irish potatoes |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |

To increase the sepctrum of action and to achieve synergistic effects, the novel cyclohexane-1,3-dione derivatives may be mixed and applied together with numerous other herbicidal active ingredients. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, etc.

It may also be useful to apply the novel compounds, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. non-phytotoxic oils and oil concentrates may also be added.

TABLE 2

Selective herbicidal action of compound no. 19 and comparative agent A on postemergence application in the greenhouse

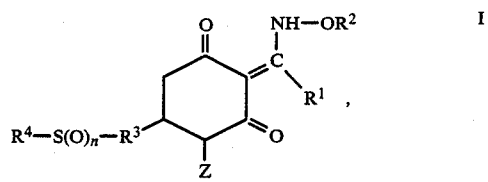

| | Percentage damage at 0.25 kg/ha | |
|---|---|---|
| Test plants | no. 19 | A (prior art) |
| Glycine max. | 0 | 0 |
| Hordeum vulgare | 0 | 90 |
| Triticum aestivum | 0 | 90 |
| Alopecurus myosuroides | 90 | 95 |
| Avena fatua | 90 | 95 |
| Lolium multiforum | 90 | 98 |

We claim:

1. A cyclohexane-1,3-dione derivative of the formula

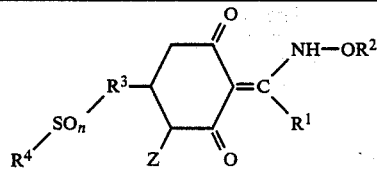

wherein $R^1$ is alkyl of from 2 to 4 carbon atoms, $R^2$ is vinyl or allyl, $R^3$ is ethylene or 1,2-propylidene, $R^4$ is phenylethyl, Z=H, and n is O, or a salt thereof.

2. A herbicide for combating grasses in broad-leaved crops and monocotyledon crops, which do not belong to the family of grasses (Gramineae), and in cereals, which comprises: a carrier or diluent and, as active ingredient, an effective amount of a cyclohexane-1,3-dione derivative as defined in claim 1.

3. A process for combating grasses in broad-leaved crops and monocotyledon crops, which do not belong to the family of grasses (Gramineae), and in cereals which comprises: treating the grasses with from 0.05 to 5 kg/ha of a compound as defined in claim 1.

* * * * *

TABLE 1

Herbicidal action of compounds according to the invention on pre- and postemergence application of 3.0 kg/ha in the greenhouse.

| | | | | | | | Test plants and % damage | | | |
|---|---|---|---|---|---|---|---|---|---|---|
| | | | | | | | Preemergence | | Postemergence | |
| Compound no. | $R^1$ | $R^2$ | —S—$R^3$— | n | $R^4$ | Z | Echinochloa crus-galli | Lolium multi-florum | Echinochloa crus-galli | Lolium multi-florum |
| 11 | n-$C_3H_7$ | —$C_2H_5$ | S—CH(CH$_3$)—CH$_2$— | 0 | $C_6H_5$—CH$_2$—CH$_2$— | H | 100 | 100 | 100 | 90 |
| 12 | n-$C_3H_7$ | —CH$_2$CH=CH$_2$ | " | 0 | " | H | 100 | 100 | 100 | 90 |
| 3 | n-$C_3H_7$ | —$C_2H_5$ | " | 0 | CH$_2$=CH—CH$_2$— | H | 100 | 100 | 100 | 100 |
| 4 | n-$C_3H_7$ | —CH$_2$CH=CH$_2$ | " | 0 | " | H | 100 | 100 | 100 | 100 |